| (12) | United States Patent | (10) Patent No.: | US 6,971,259 B2 |
|---|---|---|---|
| | Gysling | (45) Date of Patent: | Dec. 6, 2005 |

(54) FLUID DENSITY MEASUREMENT IN PIPES USING ACOUSTIC PRESSURES

(75) Inventor: Daniel L. Gysling, Glastonbury, CT (US)

(73) Assignee: Weatherford/Lamb, Inc., Houston, TX (US)

(*) Notice: Subject to any disclaimer, the term of this patent is extended or adjusted under 35 U.S.C. 154(b) by 186 days.

(21) Appl. No.: 10/010,183

(22) Filed: Nov. 7, 2001

(65) Prior Publication Data

US 2003/0084707 A1 May 8, 2003

(51) Int. Cl.⁷ ............................................... G01N 9/36
(52) U.S. Cl. ................................... 73/32 A; 73/24.05
(58) Field of Search ............................. 73/32 A, 32 R, 73/24.01, 24.05, 24.06, 61.79, 61.41, 61.47, 61.49, 597, 643, 655, 656, 657

(56) References Cited

U.S. PATENT DOCUMENTS

| 3,149,492 A | 9/1964 | Weinberg |
| 3,851,521 A | 12/1974 | Ottenstein |
| 4,080,837 A | 3/1978 | Alexander et al. ......... 73/61.45 |
| 4,114,439 A | 9/1978 | Fick |
| 4,144,768 A | 3/1979 | Andersson |
| 4,159,646 A | 7/1979 | Paulsen |
| 4,164,865 A | 8/1979 | Hall |

(Continued)

FOREIGN PATENT DOCUMENTS

| DE | 19511234 | 12/1999 | |
| EP | 0684458 | 5/1995 | |
| FR | 2 357 868 | 7/1976 | |
| JP | 406082281 | 9/1992 | |
| WO | WO 93/14382 | 7/1993 | |
| WO | WO 96/04528 | 2/1996 | |
| WO | WO 00/00793 | 1/2000 | |
| WO | WO 00/00799 | 1/2000 | ........... G01L/11/02 |
| WO | WO 01/01088 A1 | 1/2001 | ........... G01F/15/00 |

OTHER PUBLICATIONS

Mesch, F. (1990) "Speed and Flow Measurement by an Intelligent Correlation System", Advances in Instrumentation and Control, Research Triangle Park, NC, part 4, p. 1899–1914.

Specification for U.S. Appl. No. 09/345,827, filed Jul. 2, 1999.

(Continued)

*Primary Examiner*—Helen Kwok
(74) *Attorney, Agent, or Firm*—Moser, Patterson & Sheridan, L.L.P.

(57) ABSTRACT

The density of at least one fluid in a pipe is determined using a pair of effective sound speeds $a_{1eff}$ and $a_{2eff}$ of the fluid/pipe system. The pair of effective sound speed measurements is taken at two sensing regions along the pipe wherein each of the sensing regions has a different cross sectional area compliance. The pair of effective sound speeds $a_{1eff}$ and $a_{2eff}$ is provided to signal processing logic 60, which determines the density of the fluid flowing in the pipe. The effective sound speeds $a_{1eff}$ and $a_{2eff}$ may be provided by a pair of sound speed meters positioned at the sensing regions wherein the sound speed meters utilize a spatial array of acoustic pressure sensors placed at predetermined axial locations along the pipe. The acoustic pressure sensors measure one-dimensional planar acoustic waves that are lower in frequency (and longer wavelength) signals than those used for ultrasonic flow meters, and thus is more tolerant to inhomogeneities in the flow. In addition, no external acoustic source is required and the meters may operate using passive listening.

24 Claims, 6 Drawing Sheets

U.S. PATENT DOCUMENTS

| | | | |
|---|---|---|---|
| 4,236,406 A | 12/1980 | Reed | |
| 4,275,602 A | 6/1981 | Fujishiro | |
| 4,445,389 A | 5/1984 | Potzick | |
| 4,499,418 A | 2/1985 | Helms | |
| 4,515,473 A | 5/1985 | Mermelstein | |
| 4,520,320 A | 5/1985 | Potzick | |
| 4,546,649 A | 10/1985 | Kantor | 73/168 |
| 4,706,501 A | 11/1987 | Atkinson | |
| 4,788,852 A | 12/1988 | Martin | |
| 4,813,270 A | 3/1989 | Baillie | |
| 4,862,750 A | 9/1989 | Nice | |
| 4,864,868 A | 9/1989 | Khalifa | 73/861.24 |
| 4,884,457 A | 12/1989 | Hatton | |
| 4,896,540 A | 1/1990 | Shakkottai | |
| 4,932,262 A | 6/1990 | Wlodarczyk | |
| 4,947,127 A | 8/1990 | Helms | |
| 4,950,883 A | 8/1990 | Glenn | 250/227.14 |
| 4,976,151 A | 12/1990 | Morishita | |
| 4,996,419 A | 2/1991 | Morey | 250/227.18 |
| 5,024,099 A | 6/1991 | Lee | |
| 5,031,460 A | 7/1991 | Kanekobu | |
| 5,040,415 A | 8/1991 | Barkhoudarian | |
| 5,051,922 A | 9/1991 | Toral | |
| 5,058,437 A | 10/1991 | Chaumont | |
| 5,083,452 A | 1/1992 | Hope | 73/61 R |
| 5,099,697 A | 3/1992 | Agar | |
| 5,115,670 A | 5/1992 | Shen | 73/61.41 |
| 5,152,181 A | 10/1992 | Lew | |
| 5,207,107 A | 5/1993 | Wolf | |
| 5,218,197 A | 6/1993 | Carroll | 250/227.16 |
| 5,317,576 A | 5/1994 | Leonberger et al. | 372/6 |
| 5,321,991 A | 6/1994 | Kalotay | |
| 5,347,873 A | 9/1994 | Vander Heyden | |
| 5,359,897 A * | 11/1994 | Hamstead et al. | 73/597 |
| 5,361,130 A | 11/1994 | Kersey | |
| 5,363,342 A | 11/1994 | Layton et al. | 367/149 |
| 5,367,911 A | 11/1994 | Jewell et al. | 73/861.08 |
| 5,372,046 A | 12/1994 | Kleven | |
| 5,398,542 A | 3/1995 | Vasbinder | 73/40.5 |
| 5,401,956 A | 3/1995 | Dunphy et al. | 250/227.18 |
| 5,426,297 A | 6/1995 | Dunphy et al. | 250/227.23 |
| 5,440,932 A | 8/1995 | Wareham | |
| 5,493,390 A | 2/1996 | Varasi et al. | 356/32 |
| 5,493,512 A | 2/1996 | Peube et al. | 364/510 |
| 5,513,913 A | 5/1996 | Ball et al. | 374/120 |
| 5,546,813 A | 8/1996 | Hastings et al. | 73/861.29 |
| 5,548,530 A | 8/1996 | Baumoel | 364/509 |
| 5,564,832 A | 10/1996 | Ball | |
| 5,576,497 A | 11/1996 | Vignos | |
| 5,591,922 A | 1/1997 | Segeral et al. | 73/861.04 |
| 5,597,961 A | 1/1997 | Marrelli | |
| 5,639,667 A | 6/1997 | Heslot | |
| 5,642,098 A | 6/1997 | Santa Maria | |
| 5,644,093 A | 7/1997 | Wright | |
| 5,654,551 A | 8/1997 | Watt | |
| 5,670,720 A | 9/1997 | Clark | |
| 5,680,489 A | 10/1997 | Kersey | |
| 5,689,540 A | 11/1997 | Stephenson | |
| 5,708,211 A | 1/1998 | Jepson et al. | 73/861.04 |
| 5,719,329 A | 2/1998 | Jepson et al. | 73/61.49 |
| 5,730,219 A | 3/1998 | Tubel | |
| 5,732,776 A | 3/1998 | Tubel | |
| 5,741,980 A | 4/1998 | Hill et al. | 73/861.04 |
| 5,803,167 A | 9/1998 | Bussear | |
| 5,804,713 A | 9/1998 | Kluth | |
| 5,835,884 A * | 11/1998 | Brown | 73/861.27 |
| 5,842,347 A | 12/1998 | Kinder | |
| 5,845,033 A | 12/1998 | Berthold et al. | 385/12 |
| 5,906,238 A | 5/1999 | Carmody | |
| 5,907,104 A | 5/1999 | Cage | |
| 5,908,990 A | 6/1999 | Cummings | |
| 5,925,821 A | 7/1999 | Bousquet | |
| 5,925,879 A | 7/1999 | Hay | |
| 5,939,643 A | 8/1999 | Oertel | |
| 5,956,132 A | 9/1999 | Donzier | |
| 5,959,547 A | 9/1999 | Tubel | |
| 5,963,880 A | 10/1999 | Smith | |
| 5,975,204 A | 11/1999 | Tubel | |
| 5,992,519 A | 11/1999 | Ramakrishnan | |
| 5,996,690 A | 12/1999 | Shaw | |
| 6,002,985 A | 12/1999 | Stephenson | |
| 6,003,383 A | 12/1999 | Zielinska | |
| 6,003,385 A | 12/1999 | De Vanssay | |
| 6,009,216 A | 12/1999 | Pruett | |
| 6,016,702 A | 1/2000 | Maron | |
| 6,158,288 A | 12/2000 | Smith | 73/861.25 |
| 6,202,494 B1 * | 3/2001 | Rebel et al. | 73/861.29 |
| 6,216,532 B1 | 4/2001 | Stephenson | |
| 6,233,374 B1 | 5/2001 | Ogle | |
| 6,279,660 B1 | 8/2001 | Hay | |
| 6,349,599 B1 * | 2/2002 | Lynnworth et al. | 74/644 |
| 6,354,147 B1 | 3/2002 | Gysling | |
| 6,371,982 B2 * | 4/2002 | Berg et al. | 623/1.4 |
| 6,442,996 B1 * | 9/2002 | Thurston et al. | 73/24.01 |
| 6,446,494 B2 * | 9/2002 | Hastings et al. | 73/54.41 |
| 6,450,037 B1 * | 9/2002 | McGuinn et al. | 73/705 |
| 6,502,465 B1 * | 1/2003 | Vedapuri et al. | 73/861.04 |

OTHER PUBLICATIONS

Specification for U.S. Appl. No. 09/346,607, filed Jul. 2, 1999.

Specification for U.S. Appl. No. 09/740,760, filed Nov. 29, 2000.

Specification for U.S. Appl. No. 09/326,097, filed Jun. 4, 1999.

Specification for U.S. Appl. No. 09/519,785, filed Mar. 7, 2000.

Specification for U.S. Appl. No. 09/346,606, filed Jul. 2, 1999.

Specification for U.S. Appl. No. 09/346,605, filed Jul. 2, 1999.

Specification for U.S. Appl. No. 09/344,069, filed Jun. 25, 1999.

Gysling, D. (1999) "Development of a Fiber Optic Downhole Multiphase Flow Meter", in "Field Applications & New Technologies for Multiphase Metering", Multiphase Technology Series Conference, Aberdeen, Scotland.

Beranek, L. and Ver, I. (1992) in "Noise and Vibration Control Engineering, Principles and Application", John Wiley & Sons, Inc., Chapter 14, p:537–541.

Dowling, A. and Williams, J. in "Sound and Sources of Sound", Ellis Horwood Limited, Section 4, p: 79–80.

Kersey, A. et al. (1993) "Multiplexed Fiber Bragg Grating Strain–Sensor System with a Fiber Fabry–Perot Wavelength Filter", Optics Letters, 18:1370–1372.

Dandridge, A. & Cogdell, G. (1991) "Fiber Optic Sensors for Navy Applications", IEEE, LCS, 2:81–89.

Nielsen, R. (1991) "Sonar Signal Processing", Artech Huse Inc., Chapter 2, p:51–59.

Krim A. and Viberg M. (1996) "Two Decades of Array Signal Processing Research", IEEE Signal Processing Magazine, p:67–94.

Kersey A. and Darkin, J., Editors (1992) SPIE vol. 1586, "Distributed and Multiplexed Fiber Optic Sensors", p:1–243.

Nerby et al. "A cost effective technique for production well testing", (1995) Offshore Technology Conference, p:505–515.

"Noise and Vibration Control Engineering Principles and Applications", Leo L. Beranek and Istvan L. Ver, A Wiley Interscience Publication, pp. 537–541.

"Development of a Fiber Optic Downhole Multiphase Flow Meter", Daniel L. Gysling, 5$^{th}$ Inter. Conference– Multiphase Technology Series, Feb. 1999, Aberdeen, Scotland.

"Sound and Sources of Sound", by A.P. Dowling and J.E. Williams, pp. 224–229.

"Speed and Flow Measurement by an Intelligent Correlation System" by Franz Mesch, Advances in Instrumentation and Control, 45 (1990) Part 4. Research Triangle Park, NC, US.

U.S. Appl. No. 09/346,607, filed Jul. 2, 2000, Gysling et al.
U.S. Appl. No. 09/345,827, filed Jul. 2, 1999, Gysling et al.
U.S. Appl. No. 09/346,606, filed Jul. 2, 1999, Gysling et al.
U.S. Appl. No. 09/346,604, filed Jul. 2, 1999, Gysling et al.
U.S. Appl. No. 09/346,605, filed Jul. 2, 1999, Gysling et al.
U.S. Appl. No. 09/344,094, filed Jun. 25, 1999, Gysling et al.
U.S. Appl. No. 09/519,785, filed Mar. 7, 2000, Gysling et al.
U.S. Appl. No. 09/326,097, filed Jun. 4, 1999, Ogle et al.
PCT International Search Report, International Application No. PCT/GB02/05004, dated Feb. 13, 2003.

* cited by examiner

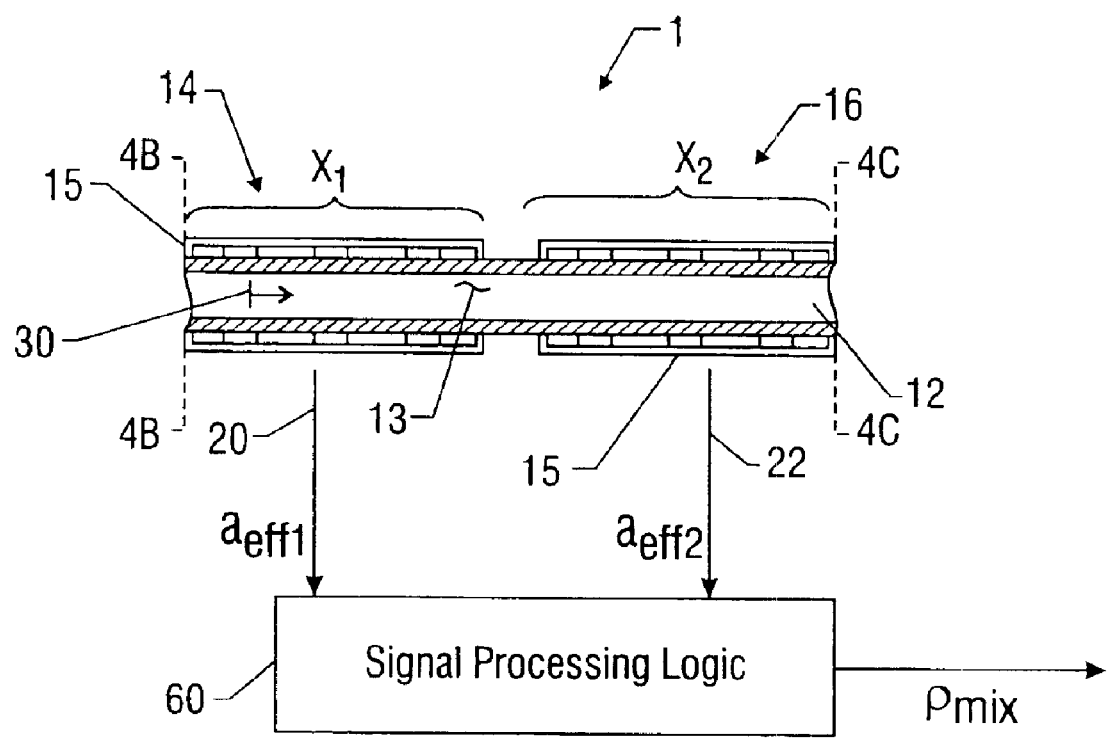
FIG. 4A
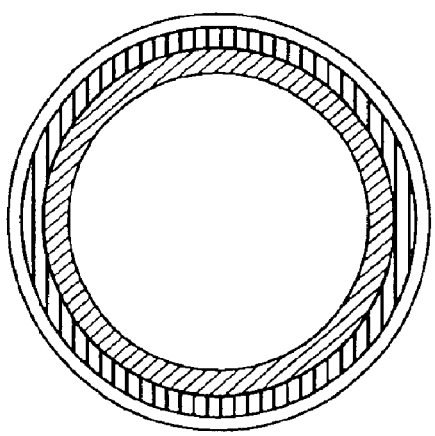
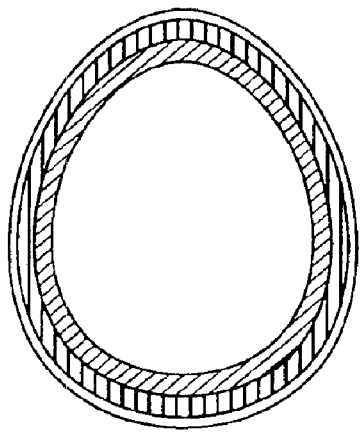
FIG. 4B  FIG. 4C

FLUID DENSITY MEASUREMENT IN PIPES USING ACOUSTIC PRESSURES

CROSS REFERENCES TO RELATED APPLICATIONS

This application contains subject matter related to that disclosed in U.S. patent applications Ser. No. 09/344,094, entitled "Fluid Parameter Measurement in Pipes Using Acoustic Pressures," filed Jun. 25, 1999; Ser. No. 09/344,070, entitled "Measurement of Propagating Acoustic Waves in Compliant Pipes," filed Jun. 25, 1999; Ser. No. 09/344,069, entitled "Displacement Based Pressure Sensor Measuring Unsteady Pressure in a Pipe," filed Jun. 25, 1999; and Ser. No. 09/344,093, entitled "Non-Intrusive Fiber Optic Pressure Sensor for Measuring Unsteady Pressures within a Pipe," filed Jun. 25, 1999, all of which are incorporated herein by reference.

TECHNICAL FIELD

This invention relates to fluid parameter measurement in pipes and more particularly to measuring speed of sound and density of fluids in pipes using acoustic pressures. The measurement exploits the interaction between pipe flexibility, speed of sound propagation, and density of the fluid within a conduit.

BACKGROUND ART

It is well known that by measuring the speed of sound ($a_{mix}$) of a fluid in a pipe, various parameters of the fluid may be determined, such as is described in U.S. Pat. No. 4,080,837, entitled "Sonic Measurement of Flow Rate and Water Content of Oil-Water Streams," to Alexander et al.; U.S. Pat. No. 5,115,670, entitled "Measurement of Fluid Properties of Two-Phase Fluids Using an Ultrasonic Meter," to Shen; and U.S. Pat. No. 4,114,439, entitled "Apparatus for Ultrasonically Measuring Physical Parameters of Flowing Media," to Fick. Such techniques utilize a pair of acoustic transmitters/receivers (transceivers) to generate a sound signal and to measure the time it takes for the sound signal to travel between the transceivers. This is also known as a "sing-around" or "transit time" method. However, such techniques require precise control of the acoustic source and are costly and/or complex to implement via electronics.

Also, these techniques use ultrasonic acoustic signals as the sound signals, which are high frequency, short wavelength signals (i.e., wavelengths that are short compared to the diameter of the pipe). Typical ultrasonic devices operate near 200 kHz, which corresponds to a wavelength of about 0.3 inches in water. In general, to allow for signal propagation through the fluid in an unimpeded and thus interpretable manner, the fluid should be homogeneous down to scale lengths of several times smaller than the acoustic signal wavelength. Thus, the criterion for homogeneity of the fluid becomes increasingly more strict with shorter wavelength signals. Consequently, inhomogeneities in the fluid, such as bubbles, gas, dirt, sand, slugs, stratification, globules of liquid, and the like, will reflect or scatter the transmitted ultrasonic signal. Such reflection and scattering inhibit the ability of the instrument to determine the propagation velocity. For this reason, the application of ultrasonic flow meters has been limited primarily to well mixed flows.

Gamma-densitometers are widely used in the art for performing density measurements of fluids within pipes. These devices utilize a nuclear source to expose the fluids to a gamma radiation beam and measure density based on gamma beam absorption. The primary drawbacks of this type of density meter are the environmental and safety issues associated with the nuclear sources.

Another prior art method of determining the density of a fluid within a pipe is through the use of a Coriolis meter. A Coriolis meter measures mass flow and density as the primary measurements by tracking the natural frequency of a vibrating pipe filled with the fluid. These devices require a vibration source, among other elements, which make Coriolis meters mechanically complex, and relatively expensive to install and maintain.

SUMMARY OF THE INVENTION

According to the present invention, an apparatus for measuring the density of at least one fluid in a pipe comprises at least two sound speed meters disposed at different sensing regions along the pipe. Each sound speed meter measures an acoustic pressure within the pipe at a corresponding axial location, providing an effective sound speed signal indicative of the propagation velocity of a one-dimensional acoustic pressure wave traveling along the pipe at each of the sound speed meters ($a_{1eff}$ and $a_{2eff}$). A signal processor, responsive to the sound speed signals, provides a signal indicative of the density of the fluid in the pipe.

According further to the present invention, the cross sectional compliance of the two sensing regions is substantially different from one another. Still further, the cross sectional geometry of the pipe is of a non-circular geometry in one of the two sensing regions.

According still further to the present invention, the sound speed meters are fiber optic based sound speed meters, and are isolated from an outside environment by a concentric shell. The shell comprises an evacuated space, or is filled with a fluid of known acoustic impedance.

The present invention provides a significant improvement over the prior art by providing a measurement of the density $\rho_{mix}$ of a mixture of one or more fluids within a pipe (where a fluid is defined as a liquid or a gas) by using an axial array of sound speed meters positioned along the pipe. An explicit acoustic noise source is not required, as the background acoustic noises within the pipe (or fluid therein) will likely provide sufficient excitation to enable characterization of the speed of sound of the mixture by merely passive acoustic listening.

The invention works with acoustic signals having lower frequencies (and thus longer wavelengths) than those used for ultrasonic meters, such as below about 20 kHz (depending on pipe diameter). As such, the invention is more tolerant to the introduction of gas, sand, slugs, or other inhomogeneities in the flow.

The present invention allows the density to be determined in a pipe independent of pipe orientation, i.e., vertical, horizontal, or any orientation therebetween. Also, the invention does not require any disruption to the flow within the pipe (e.g., an orifice or venturi). Furthermore, if fiber optic sound speed meters are used to obtain the effective sound speed measurements, which are well suited to the harsh down hole environment, such meters eliminate the need for any electronic components down hole, thereby improving reliability of the measurement.

Also, a strain gauge (optical, electrical, etc.) based sound speed meter that measures hoop strain on the pipe may be used to measure the ac pressure. Fiber optic wrapped sensors may be used as optical strain gauges to provide circumferentially averaged pressure. Thus, the present invention provides non-intrusive measurements of the density of the fluid, which enables real time monitoring and optimization for oil and gas exploration and production.

The foregoing and other objects, features, and advantages of the present invention will become more apparent in light of the following detailed description of exemplary embodiments thereof.

BRIEF DESCRIPTION OF THE DRAWINGS

FIG. 4 is a schematic block diagram of a density meter having an egg shaped cross section in one sensing region, in accordance with the present invention.

DETAILED DESCRIPTION OF THE INVENTION

Figure 1:
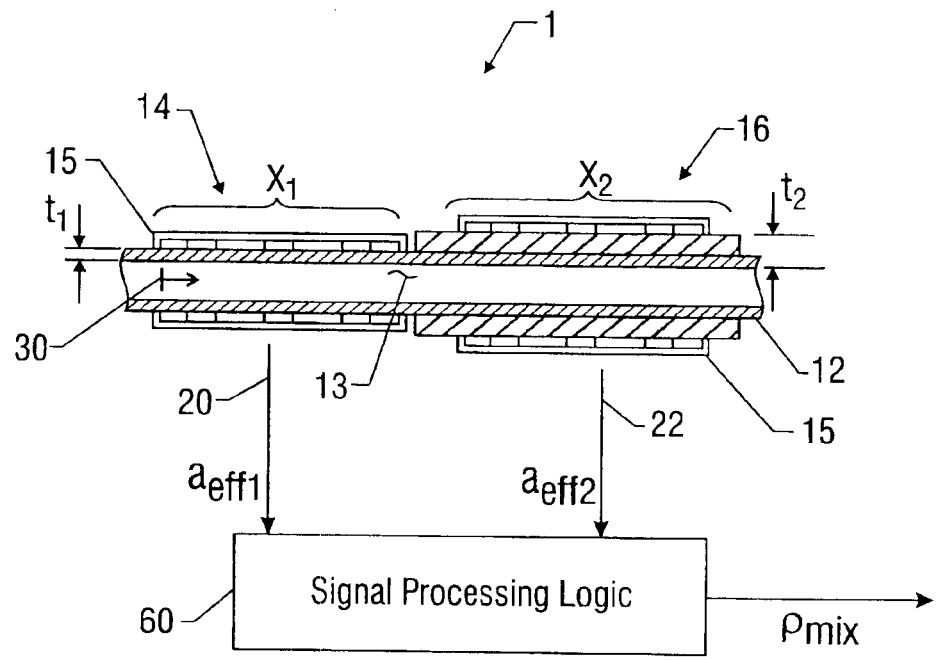
FIG. 1 is a schematic block diagram of a density meter, in accordance with the present invention.

The density meter 1 of FIG. 1 uses a pair of sound speed meters 14, 16 placed at axial locations, or sensing regions, $X_1, X_2$ along the pipe 12 for measuring the density of at least one fluid in a pipe 12. The sound speed meters 14, 16 provide the effective speed of sound $a_{1\mathit{eff}}$ and $a_{2\mathit{eff}}$ of the fluid/pipe system on lines 20, 22 which are provided to signal processing logic αwhich determines the density of the fluid (or mixture) in the pipe 12 using relationships between the compliance of the pipe and various fluid parameters as will be more fully described below. Numerous sensing and processing techniques may be employed to further determine the infinite speed of sound $a_{mix\infty}$ of the fluid in the fluid/pipe system from the measured effective speed of sound $a_{\mathit{eff}}$, such as those disclosed in U.S. patent application Ser. No. 09/344,094, entitled "Fluid Parameter Measurement in Pipes Using Acoustic Pressures," filed Jun. 25, 1999, the disclosure of which is incorporated herein by reference in its entirety.

Some or all of the functions within the logic 60 may be implemented in software (using a microprocessor or computer) and/or firmware, or may be implemented using analog and/or digital hardware, having sufficient memory, interfaces, and capacity to perform the functions described.

The effective speeds of sound $a_{1\mathit{eff}}$ and $a_{2\mathit{eff}}$ are provided to logic 60 wherein the logic calculates the density of the fluid from the difference in the effective sound speeds as will be more fully described below. Sound speed meters 14, 16 utilize acoustic pressure signals that, as measured, are lower frequency (and longer wavelength) signals than those used for ultrasonic flow meters of the prior art, as explained in the incorporated '094 application. Thus, the current invention is more tolerant to inhomogeneities in the flow.

The typical frequency range for acoustic pressure signals of the present invention is from about 10 Hz to about 10,000 Hz. The acoustic pressure signals are generated within the fluid of the pipe 12 by a variety of non-discrete sources such as remote machinery, pumps, valves, elbows, as well as the fluid flow itself. It is this last source, the fluid flowing within the pipe, that is a generic source of acoustic noise that assures a minimum level of acoustics for any fluid/pipe systems for which the present invention takes unique advantage. The flow generated acoustics increase with mean flow velocity and the overall noise levels (acoustic pressure levels) are a function of the generating mechanism and the damping mechanism. Experience indicates that pipe systems typically have sufficient ambient noise levels of 100 to 180 dbA.

No external discrete noise source is required within the present invention and thus may operate using passive listening. It is within the scope of the present invention that the sound speed meter or sensor 14, 16 spacing may be known or arbitrary and that as few as two sensors are required if certain information is known about the acoustic properties of the system as will be more fully described below.

As is known and as is described in the references incorporated herein, planar compression waves 30 propagating within a fluid contained within a conduit 12 exert an unsteady internal pressure loading on the conduit. The degree to which the conduit displaces as a result of the unsteady pressure loading influences the speed of propagation of the compression wave 30 within the fluid/pipe system. For a given fluid, the more compliant the conduit, the greater the reduction of the propagation velocity of the compression wave. Also, for a given pipe stiffness, the denser the fluid and the higher the inifinite domain sound speed, i.e., the speed of sound in an unbounded media, the greater the reduction in the speed of sound due to the pipe flexibility or compliance. More specifically, the relationship between the infinite domain sound speed ($a_{mix\infty}$), density ($\rho_{mix}$) of a fluid, the elastic modulus of the pipe (E), thickness of the pipe (t), the radius of a vacuum-backed cylindrical conduit (R), and the effective propagation velocity ($a_{\mathit{eff}}$) for a one dimensional compression wave is given by the following expression:

$$a_{\mathit{eff}} = \frac{1}{\sqrt{\frac{1}{a_{mix\infty}^2} + \rho_{mix}\frac{2R}{Et}}} \qquad \text{(Eq. 1)}$$

Figure 2:
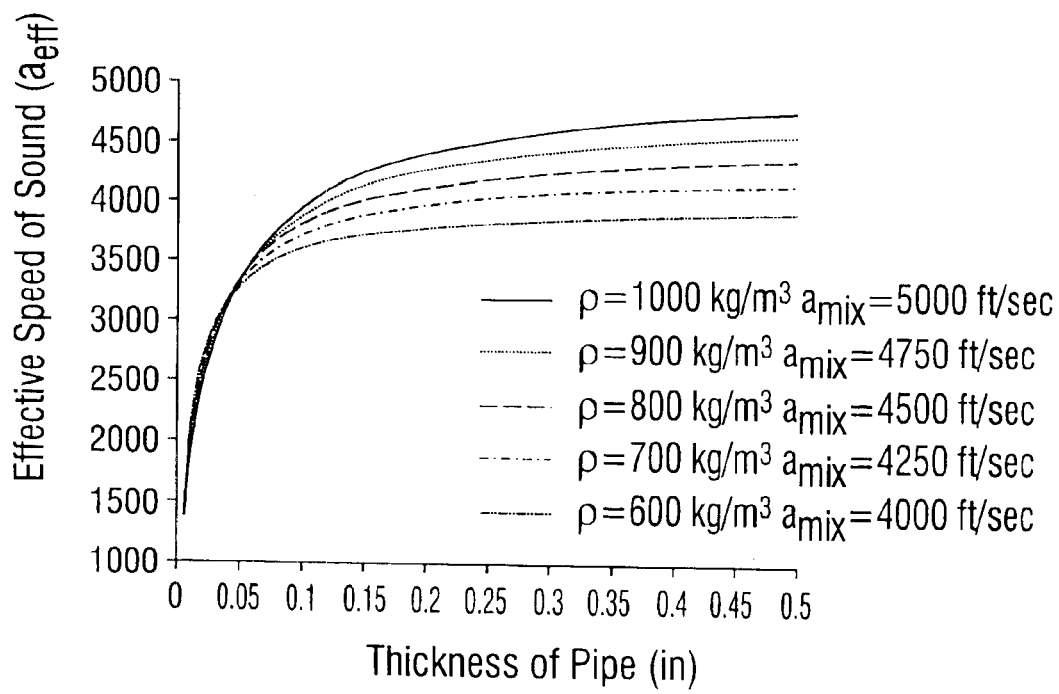
FIG. 2 is a graphical representation of the effective speed of sound of a fluid/pipe system for various pipe wall thicknesses, in accordance with the present invention.

FIG. 2 shows the effective propagation velocity, or effective sound speed for a specific example of the density meter 1 of FIG. 1 in accordance with the present invention. In this particular embodiment, the effective sound speed is shown for a fluid contained in a vacuum-backed, cylindrical steel conduit with acoustic propagation velocities and density representative of hydrocarbon liquid and water mixtures as typically found in the oil and gas industry. FIG. 2 shows the effect of varying the compliance of the pipe/fluid system by changing the wall thickness of a 5.50 inch OD steel pipe from some theoretical minimum value to a thickness of 0.5 inches for five different fluids having densities from 600 to 1000 kg/m³. As shown in FIG. 2, varying the thickness of the pipe has a significant effect on the effective speed of sound of the fluid/pipe system. For simplicity sake, the present invention is described with regard to particular embodiments comprising vacuum-backed conduits having sufficiently low frequencies (compared to breathing mode and resonant frequencies) such that the pertinent dynamical response is captured by the static compliance of the conduit. The conduit may be vacuum backed by a concentric shell 15 (FIG. 1) or other suitable structure to isolate the sensing regions $X_1$, $X_2$ from the outside environment. In alternative embodiments, the sensing regions $X_1$, $X_2$ may be isolated within the concentric shell 15 by a known fluid or air. It is important that a static fluid having lower acoustic impedance than the fluid flowing within the pipe surround the sound speed meters. The advantages and effect of the vacuum backed conduit, as well as other isolation techniques, are described in U.S. patent application Ser. No. 09/344,070, entitled "Measurement of Propagating Acoustic Waves in Compliant Pipes," filed Jun. 25, 1999, which is incorporated herein by reference in its entirety.

Equation 1 can be generalized in terms of the cross-sectional area compliance ($\sigma_{conduit}$) of the conduit and the infinite sound speed, the density of the fluid, and the effective sound speed of the pipe/fluid system as given by:

$$\frac{1}{\rho_{eff} a_{eff}^2} = \frac{1}{\rho_{mix} a_{mix_\infty}^2} + \sigma_{conduit} \quad \text{(Eq. 2)}$$

The cross sectional area compliance is a measure of the increase in cross-sectional area of a conduit for a given increase in internal pressure as set forth in the following relationship:

$$\sigma_{conduit} = \frac{\partial A_{cross\ section}}{\partial P} \quad \text{(Eq. 3)}$$

For a vacuum-backed, circular cross-section pipe of elastic modulus E, having an outside radius R, and wall thickness t, the conduit compliance is given by:

$$\sigma_{conduit} = \frac{2R}{Et} \quad \text{(Eq. 4)}$$

It is important to note that, in general, the cross sectional area compliance of the fluid/pipe system can be a complex function of frequency and amplitude and can depend on all elements acoustically coupled to the conduit. For example, if an additional fluid surrounded the conduit, the acoustic properties of the surrounding fluid would influence the cross sectional area compliance presented to the compressional waves propagating internal to the conduit. It is for this reason that the present invention is presented in embodiments having a vacuum backed shell surrounding the sound speed meters as described above.

In accordance with the present invention, using the relationships described above, the dependence of propagation speed of compression disturbances (one dimensional, planar compression acoustic waves) on the compliance of the conduit 12 and fluid properties can be used to determine information regarding the fluid contained within the conduit, specifically, the density of the fluid.

Referring again to FIG. 1, there is shown a density meter 1 in which the speed of sound of an unknown fluid 13 is measured within two regions $X_1$, $X_2$, and in which the pipe 12 has differing cross sectional area compliances associated with the two regions. A first effective speed of sound $a_{eff1}$ of the fluid/pipe system is determined from an array of pressure measurements provided by sensors of sound speed meter 14. A second speed of sound $a_{eff2}$ of the fluid/pipe system is determined from an array of pressure measurements provided by sensors of sound speed meter 16. As will be more fully described below, the change in propagation velocity of one dimensional acoustic waves between the two regions $X_1$, $X_2$, along with knowledge of the cross sectional compliances of each section, provides a means to determine the density of the fluid 13. As illustrated in this example, the variation in the cross sectional compliance could be achieved through a change in the conduit compliance, e.g., through a change in wall thickness of the pipe. Other methods to vary the cross sectional area compliance are described below, and any known method of varying the cross sectional area compliance is contemplated by the present invention.

Figure 3:
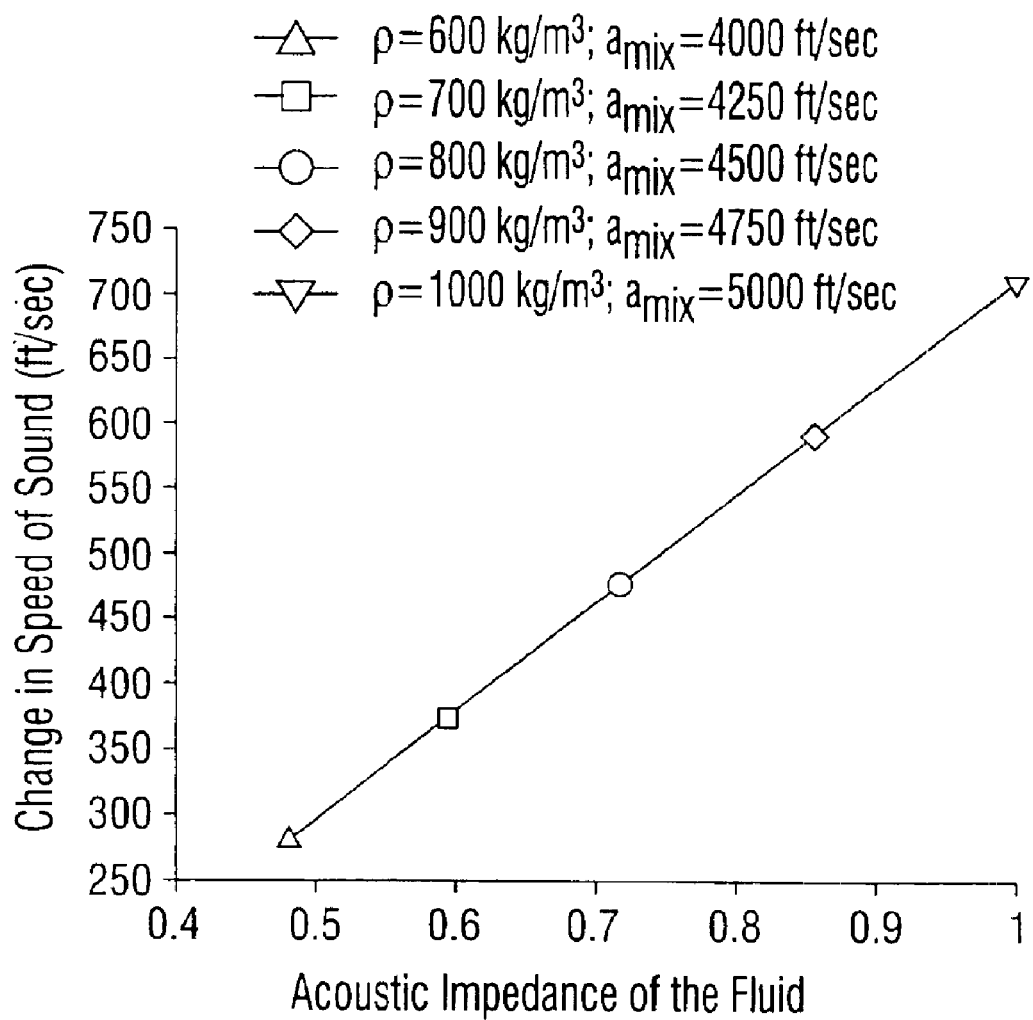
FIG. 3 is a graphical representation of the change in effective speed of sound of a fluid/pipe system for various fluid compliances, in accordance with the present invention.

The invention will now be described with attention to another specific embodiment commonly found in the oil and gas industry with reference to FIGS. 1 and 3, wherein varying the fluid compliance varies the cross sectional area compliance. In this exemplary embodiment the pipe 12 is comprised of a single material type, Inconel for example, have a wall thickness $t_1$ at region $X_1$ of 0.10 inches and a wall thickness of $t_2$ at region $X_2$ of 0.35 inches. The pipe is vacuum backed with a shell 15 that isolates the sound speed meters from the outside environment. As best shown in FIG. 3, the change in sound speed for fluid mixtures, such as representative hydrocarbon and water mixtures having densities ranging from 600 to 1000 kg/m³, is quite dramatic. As shown, the change in sound speed scales with the acoustic impedance of the fluid. For the least dense fluid with the slowest infinite medium sound speed (representing a light hydrocarbon), the change in wall thickness results in approximately 300 ft/sec change in sound speed. For the densest, highest infinite medium sound speed (representing, for example, a high watercut mixture), the change in wall thickness results in a 750 ft/sec change in sound speed. The expression for the change in effective speed of sound between two sections of vacuum-backed conduits differing only in wall thickness, where $a_o$ is the speed of sound of the fluid and $\rho_o$ is the density of the fluid is given by:

$$a_{eff_1} - a_{eff_2} = \frac{1}{\sqrt{\frac{1}{a_0^2} + \rho_o \frac{2R}{Et_1}}} - \frac{1}{\sqrt{\frac{1}{a_0^2} + \rho_o \frac{2R}{Et_2}}} \quad \text{(Eq. 5)}$$

In accordance with the present invention, the density of the unknown fluid is determined by measuring two effective sound speeds in two regions with differing, but known structural properties. For example, in the cylindrical pipe 12 of FIG. 1, having a thickness $t_1$ and $t_2$ and elastic modulus E, the density $\rho_{mix}$ of the unknown fluid is given by:

$$\rho_{mix} = \left( \frac{1}{a_{eff_1}^2} - \frac{1}{a_{eff_2}^2} \right) \frac{E}{2R} \frac{t_1 t_2}{t_2 - t_1} \quad \text{(Eq. 6)}$$

As noted above, varying wall thickness is but one way to achieve a change in cross sectional area compliance, and accordingly to measure fluid density in accordance with the present invention. In general, the larger the change in cross sectional area compliance between the two (or more) regions in which the sound speed is measured, the more robust the density measurement. In addition, an increase in the number of regions, i.e. greater than two, along a pipe with varying compliance in which sound speeds are measured would give additional, redundant measurements of density. The additional data could yield a more robust or accurate overall system depending on the specific application.

One alternative method to achieve large variations in conduit compliance is best shown with reference to FIG. 4 where a first sensing region $X_1$ comprises a circular cross sectional conduit while a second sensing region $X_2$ comprises a non-circular cross sectional conduit (shown as an egg-shaped conduit by way of example). All other properties of the pipe remain equal. The circular geometry at $X_1$ represents, for a given cross section, material modulus, and wall thickness, the configuration with the lowest cross sectional area compliance. However, the geometry of the cross section of the modified sensing region at $X_2$, formed by modifying or "egging" the circular section into an oval (or other alternative shapes such as using a cross section possessing flattened sides) significantly increases the compliance of the conduit 12. In certain embodiments between sensing region $X_2$ (non-circular geometry) and sensing region $X_1$ (circular geometry) of the same wall thickness t, cross sectional area compliance ratios greater than 30 are achievable. As demonstrated above, increasing the compliance ratio of the pipe section increases the sensitivity of the density calculation by increasing the change in effective sound speed for a given fluid density.

Figure 5:
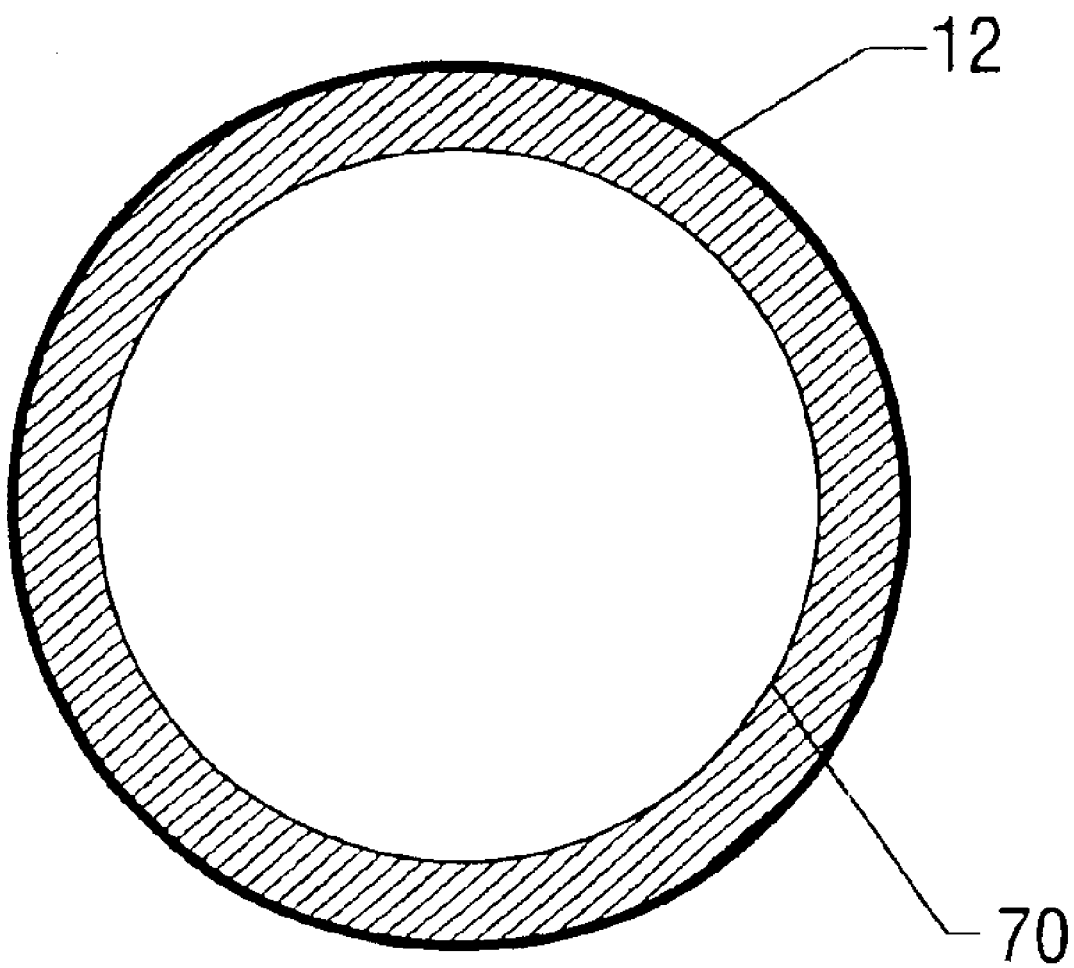
FIG. 5 is a cross sectional representation of an embodiment of a density meter having a closed cell foam liner, in accordance with the present invention.

The effective cross sectional area compliance can be modified in a variety of manners such as, by way of example, by varying materials, by incorporating wall treatments, or by incorporating resonators or cavities. Referring to FIG. 5, there is shown a modified cross sectional area compliance technique wherein a closed cell foam 70 (or other compressible liner material) is positioned along the walls of one of the sensing sections of the pipe 12 to modify the effective compliance of that section of pipe. In the embodiment shown in FIG. 5, the pipe/fluid interface would be defined as the inner surface of the liner. An increase in fluid pressure would increase the effective cross sectional area of the fluid by both compressing the foam and by expanding the pipe. It is also contemplated by the present invention that the two sensing regions may be comprised of different material types or any other variation in geometry or material property that would effectuate a difference in the compliance of the pipe between the two sensing regions.

Figure 6:
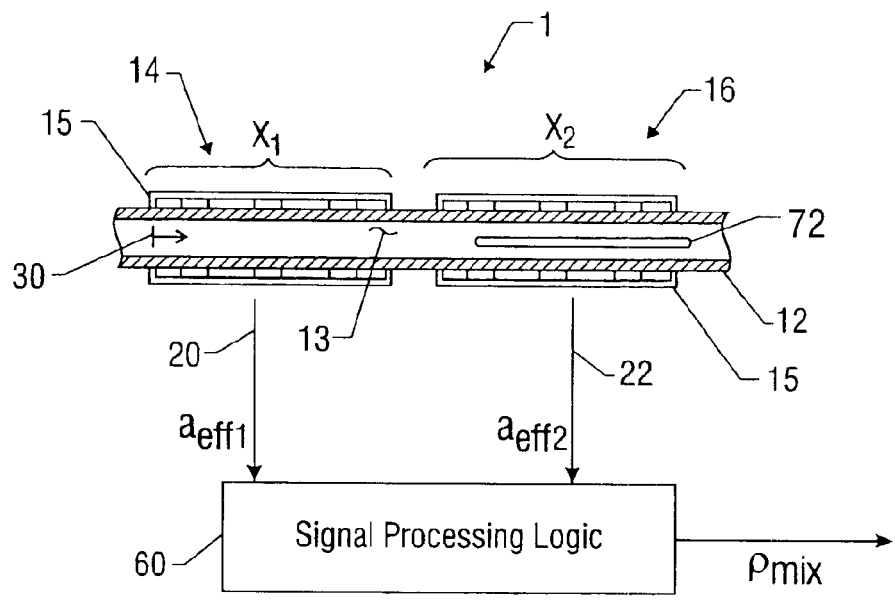
FIG. 6 is a schematic block diagram of a density meter having a tube positioned within the flow path, in accordance with the present invention.

In another example of the present invention, varying the compliance of the fluid or the area within the pipe can vary the cross sectional area compliance. For instance, and referring to FIG. 6, additional compliance could be introduced at a location along the pipe by positioning a tube 72 within the flow path along one of the sensing regions. The tube 72 would serve to modify the cross sectional compliance by compressing due to an increase in fluid pressure, which would then combine with the compliance of the pipe to modify the effective sound speed of the fluid/pipe system. Other alternatives include embodiments wherein the tube is an air filled, sealed tube (or tubes) positioned within one sensing region of the pipe.

Referring again to FIG. 1, and defining α as the ratio of conduit compliance in the "soft" section ($X_1$) to the "stiff" section ($X_2$) and where $\sigma_2$ is the cross sectional area compliance of sensing region $X_2$, the density of the fluid $\rho_{mix}$ within the meter can be expressed as:

$$\rho_{mix} = \frac{1}{(\alpha-1)\sigma_2}\left(\frac{1}{a_{eff_1}^2} - \frac{1}{a_{eff_2}^2}\right) \qquad \text{(Eq. 7)}$$

Figure 7:
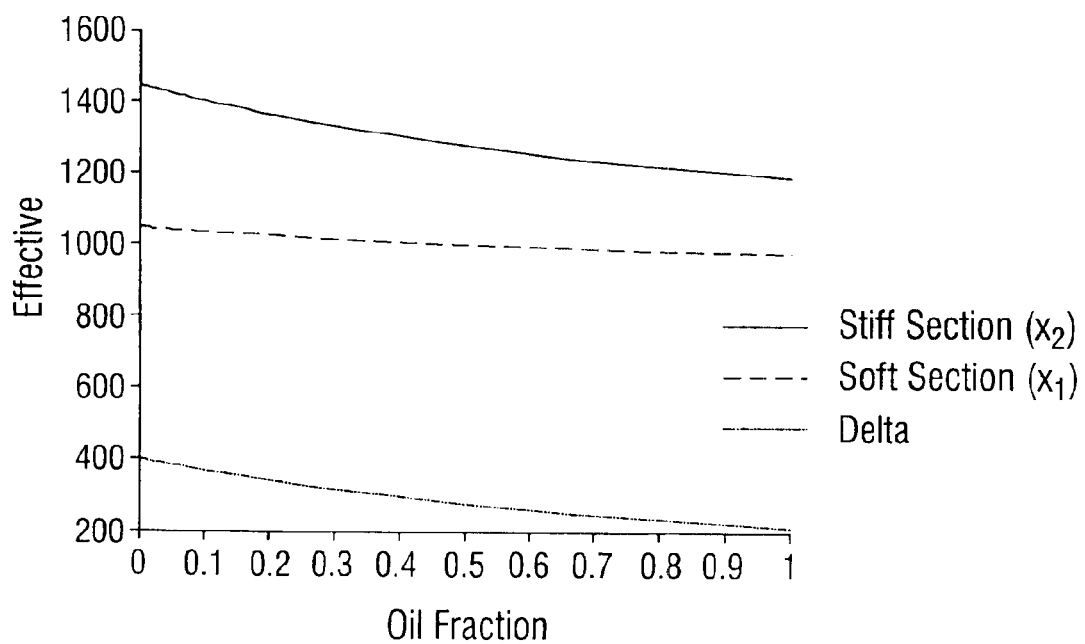
FIG. 7 is a graphical representation of the effective speed of sound of a fluid/pipe system for various volume fractions of a brine/oil mixture, in accordance with the present invention.

Referring now to FIG. 7, there is shown the fluid sound speed of a varying mixture as measured in two sensing regions $X_1$, $X_2$, of an embodiment of density meter 1 of FIG. 1. The figure shows the various effective sound speeds for oil/water mixtures varying from 0% oil to 100% oil by volume. In the example shown, the two sensing sections have a compliance ratio a of 10. As shown in FIG. 7, the difference in measured sound speed between the two sections varies from approximately 400 m/s for 100% water, to approximately 200 m/s for 100% oil. As described and depicted in the figure, the effective speed of sound as measured in the stiff section ($X_2$) is significantly higher for the mixture than that measured in the soft section ($X_1$) of the pipe 12.

In operation and referring again to FIG. 1, the two sound speed meters 14, 16 provide effective sound speeds $a_{1eff}$ and $a_{2eff}$ to signal processing logic 60, which includes the relationship set forth in equation 7. The compliance of the conduit $\rho_2$ in the second sensing region $X_2$ and the ratio of the compliances between the two sections $\sigma_1/\sigma_2$ are further provided to logic 60 to calculate the density of the mixture, $\rho_{mix}$. Thus the density of the fluid mixture can be determined without requiring specific speed of sound and calibration information concerning the fluid itself. In the embodiments described thus far, it is only required that the infinite sound speed ($a_{mix}$) and density of the fluid itself is the same in the two sections. Thus, although the density measurement described is based on speed of sound measurements, no knowledge of the infinite sound speed ($a_{mix}$) of the fluid is required to determine density.

Figure 8:
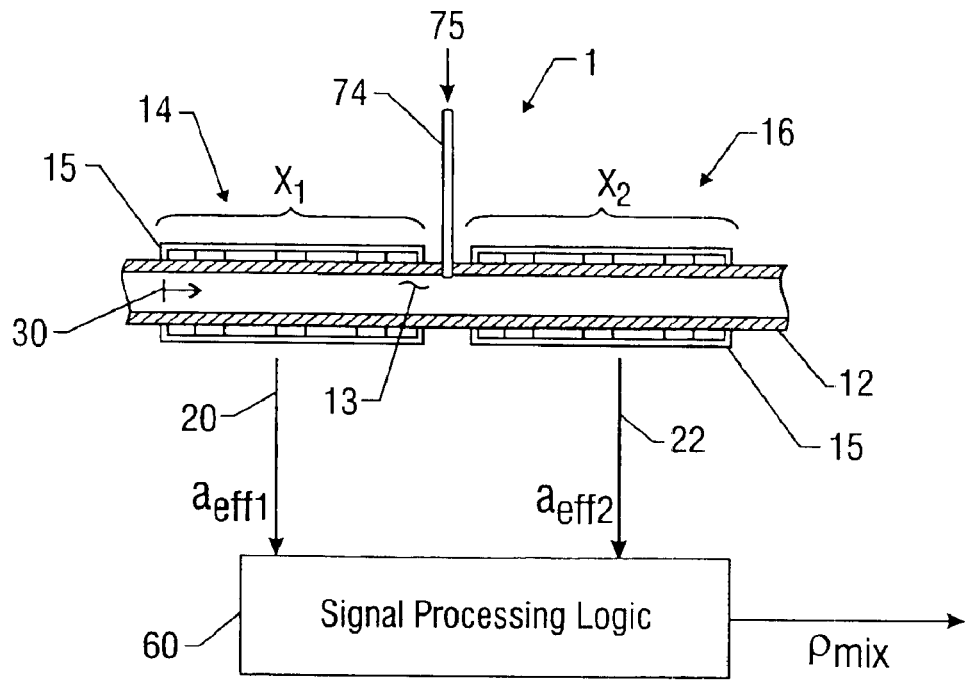
FIG. 8 is a schematic block diagram of a density meter having an input tube positioned between the sensing regions, in accordance with the present invention.

In certain other embodiments, the density of the fluid may be determined after the introduction of a known quantity of a known constituent into the fluid between the two sensing sections. Referring to FIG. 8, there is shown a density meter 1 including an input line 74 positioned between the two sensing sections $X_1$, $X_2$. In this particular embodiment the cross sectional area compliance is changed by the introduction of a constant amount of a known quantity of air 75, for example, into the fluid 13. The introduction of the air into the fluid changes the cross-sectional area compliance in the sensing region ($X_2$) downstream of input line 74. The change in compliance in the fluid due to the introduction of the air is taken into account in the relationships described above to accurately determine the density of the fluid 13.

Figure 9:
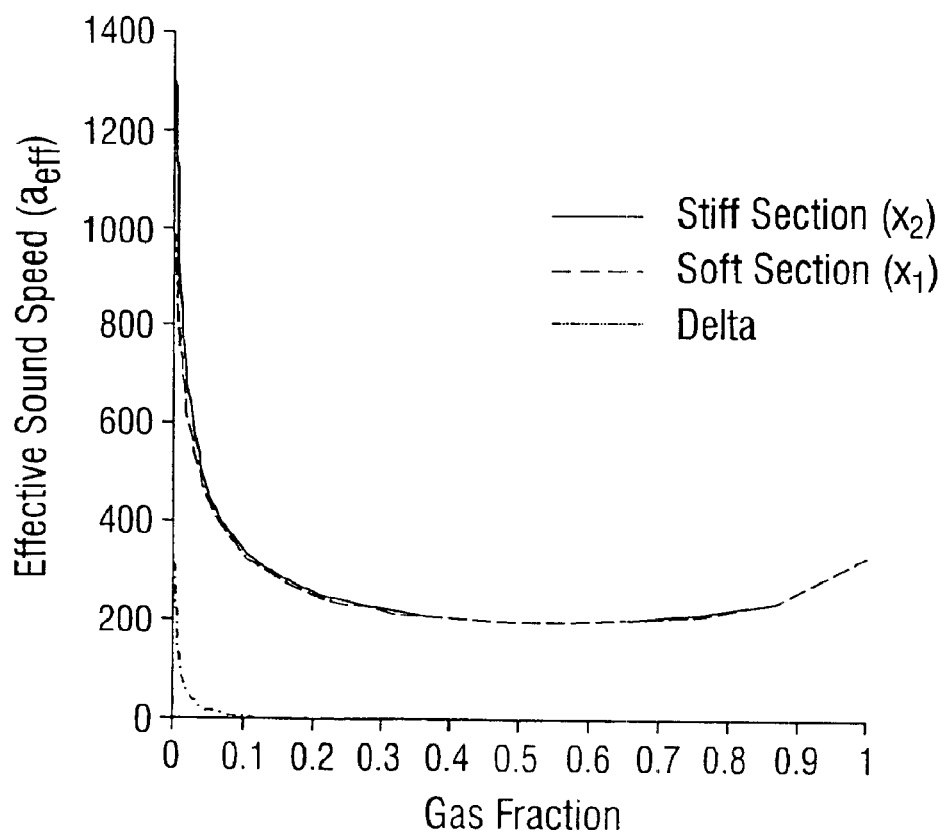
FIG. 9 is a graphical representation of the effective speed of sound of a fluid/pipe system for various volume fractions of a gas/fluid mixture, in accordance with the present invention.

In addition to liquid mixtures, the density meter of the present invention includes the ability to determine the density of gas/liquid mixtures. Referring to FIG. 9, there is shown the predicted sound speeds in the stiff ($X_2$) and soft ($X_1$) sensing regions of density meter 1 of FIG. 1 for various mixtures of gas and liquids with representative single phase compliances typical of produced gases and liquids at 100 bar. As shown, due primarily to the high compliance of the gas phase at this relatively low pressure, the change in overall sound speed in the two sections of the meter due to the change in conduit compliance is much less significant for this application than those described above. Using Equation 2, and by defining the compliance of the fluid as the inverse of the product of the fluid density and the square of the infinite dimensional sound speed, the following relation results:

$$\sigma_{mixture} \equiv \frac{1}{\rho_{mix} a_{mix_\infty}^2} \quad \text{(Eq. 8)}$$

and the ratio of the effective sound speed within the conduit to the infinite dimensional sound speed is given by:

$$\frac{a_{eff}}{a_{mix_\infty}} = \sqrt{\frac{1}{1 + \frac{\sigma_{conduit}}{\sigma_{mixture}}}} \quad \text{(Eq. 9)}$$

The change in difference in sound speed for a given change in density of the fluid is a useful metric in designing the density meter described for any specific application. Assuming that the ratio of the cross sectional compliance introduced by the structure over that of the fluid is much less than 1, this performance metric can be expressed as follows:

$$\frac{\partial (a_{1_{eff}} - a_{2_{eff}})}{\partial \rho} = \frac{a_{mix_\infty}}{\rho_{mix}} \frac{\sigma_{Stiff}}{\sigma_{mixture}} \frac{1}{2}(\alpha - 1) \quad \text{(Eq. 10)}$$

As shown, effectiveness of the density meter of the present invention described scales with both the ratio of the compliances of the two conduits as well as with the ratio of the compliance of conduit to that of the fluid. Thus, the density meter of the present invention is more effective when the cross sectional area compliance contributed by the conduit is a significant fraction of that contributed by the fluid and the ratio of the cross sectional area compliance of the two regions is significantly greater than one.

It should be understood that any of the features, characteristics, alternatives or modifications described regarding a particular embodiment may also be applied, used, or incorporated with any other embodiment described.

Although the invention has been described and illustrated with respect to exemplary embodiments thereof, the foregoing and various other additions and omissions may be made therein and thereto without departing from the spirit and scope of the present invention.

What is claimed is:

1. An apparatus for determining the density of at least one fluid within a pipe, the apparatus comprising:
    a first sound speed meter positioned at a first sensing region along the pipe which provides a first system effective sound speed signal;
    a second sound speed meter positioned at a second sensing region along the pipe which provides a second system effective sound speed signal;
    a signal processor, responsive to the first and the second system effective sound speed signals, which provides a density signal indicative of the density of the fluid within the pipe based on a calculation that includes the first and the second system effective sound speed signals, and
    wherein the first sensing region has a first compliance and wherein the second sensing region has a second compliance and wherein the first and second compliances are different.

2. The apparatus of claim 1, wherein the first sensing region has a first cross sectional compliance and wherein the second sensing region has a second cross sectional compliance and wherein the cross sectional compliances are substantially different.

3. The apparatus of claim 1, further comprising a concentric shell positioned around each of the first and the second sound speed meters thereby isolating the first and the second speed meters from an outside environment.

4. The apparatus of claim 1, wherein the first and the second sound speed meters respectively provide the first and second system effective sound speed signals from one-dimensional acoustic pressure waves traveling along the pipe.

5. The apparatus of claim 1, wherein at least one of the first and the second sound speed meters comprises a fiber optic based sound speed meter.

6. The apparatus of claim 2, wherein the first or the second sensing region of the pipe comprises a non-circular cross sectional geometry.

7. The apparatus of claim 6, wherein the non-circular cross sectional geometry comprises an oval shape.

8. The apparatus of claim 2, further comprising an input line positioned between the first and the second sensing regions to provide a substance into the fluid.

9. A method for measuring the density of a fluid within a pipe, the method comprising:
    a) measuring a first effective system sound speed at a first sensing region with a first compliance along the pipe and providing a first effective system sound speed signal;
    b) measuring a second effective system sound speed at a second sensing region with a second compliance different from the first compliance along the pipe and providing a second effective system sound speed signal; and
    c) calculating the density using the first and the second effective system sound speed signals.

10. The method of claim 9, wherein the calculating step (c) comprises:
    d) subtracting the first and the second effective system sound speed signals to obtain a difference related to a compliance difference between the first and second sensing regions.

11. The method of claim 9, wherein the measuring steps (a) and (b) comprise measuring a propagation velocity of a one-dimensional acoustic pressure wave traveling through the fluid.

12. The method of claim 10, wherein the measureing steps (a) and (b) comprise a propagation velocity of a one-dimensional acoustic pressure was traveling through the fluid.

13. The apparatus of claim 1, further comprising a tube positioned along either the first sensing region or the second sensing region and within a flow path of the fluid within the pipe.

14. An apparatus for determining the density of at least one fluid within a pipe, the apparatus comprising:
    a first meter positioned at a first sensing region along the pipe;
    a second meter positioned at a second sensing region along the pipe;
    a signal processor, responsive to signals from the first and the second meters, which provides a density signal indicative of the density of the fluid within the pipe based on a calculation that includes the signals from both the first and second meters; and
    wherein the first sensing region has a first compliance and wherein the second sensing region has a second compliance and wherein the first and second compliances are different.

15. The apparatus of claim 14, wherein the first sensing region has a first cross sectional compliance and wherein the second sensing region has a second cross sectional compliance and wherein the cross sectional compliances are substantially different.

16. The apparatus of claim 14, wherein the first and the second meters respectively provide first and second system effective sound speed signals from one-dimensional acoustic pressure waves traveling along the pipe.

17. The apparatus of claim 14, wherein the at least one of the first and the second meters comprises a fiber optic based sound speed meter.

18. The apparatus of claim 14, wherein the first or the second sensing region of the pipe comprises a non-circular cross sectional geometry.

19. The apparatus of claim 14, further comprising an input line positioned between the first and the second sensing regions to provide a substance into the fluid.

20. The apparatus of claim 14, further comprising a tube positioned along either the first sensing region or the second sensing region and within a flow path of the fluid within the pipe.

21. A method for measuring the density of a fluid within a pipe, the method comprising:

a) measuring a first parameter at a first sensing region with a first compliance along the pipe;

b) measuring a second parameter at a second sensing region with a second compliance different from the first compliance along the pipe; and c) calculating the density of the fluid using the first and the second parameters.

22. The method of claim 21, wherein the calculating step (c) comprises:

d) subtracting first and second effective system sound speed signals to obtain a difference related to a compliance difference between the first and second sensing regions.

23. The method of claim 21, wherein the measuring steps (a) and (b) comprise measuring a propagation velocity of a one-dimensional acoustic pressure wave traveling through the fluid.

24. The method of claim 21, wherein the measuring steps (a) and (b) comprise measuring a strain of the pipe.

* * * * *